United States Patent
Kondo et al.

[11] Patent Number: 5,906,582
[45] Date of Patent: *May 25, 1999

[54] ORGANISM INFORMATION MEASURING METHOD AND ARM WEAR TYPE PULSE-WAVE MEASURING METHOD

[75] Inventors: Yutaka Kondo; Katsuyuki Honda, both of Suwa; Masayuki Kawata, Chiba, all of Japan

[73] Assignees: Seiko Epson Corporation; Seiko Instruments, Inc., both of Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/527,231

[22] Filed: Sep. 12, 1995

[30] Foreign Application Priority Data

Sep. 14, 1994 [JP] Japan .................................. 6-220371

[51] Int. Cl.⁶ ...................................................... A61B 5/02
[52] U.S. Cl. .......................... 600/500; 600/502; 600/503; 600/479
[58] Field of Search ................................ 128/633, 664–7, 128/690; 356/39–41; 600/310, 322, 324, 340, 388–391, 473, 476, 479, 480, 481, 485, 500, 502, 503

[56] References Cited

U.S. PATENT DOCUMENTS

| | | | |
|---|---|---|---|
| 3,482,565 | 12/1969 | Gowen | 600/480 |
| 3,704,706 | 12/1972 | Herczfeld et al. | 128/666 |
| 3,769,974 | 11/1973 | Smart et al. | 128/666 |
| 3,871,362 | 3/1975 | Dunegan | 128/666 |
| 4,091,803 | 5/1978 | Pinder | 600/503 |
| 4,258,719 | 3/1981 | Lewyn | 600/503 |
| 4,280,506 | 7/1981 | Zurcher | 128/690 |
| 4,608,990 | 9/1986 | Elings | 128/633 |
| 4,807,639 | 2/1989 | Shimizu et al. | 600/503 |
| 5,170,786 | 12/1992 | Thomas et al. | 600/310 |
| 5,353,790 | 10/1994 | Jacques et al. | 128/633 |
| 5,423,327 | 6/1995 | Clauson et al. | 128/633 |
| 5,523,589 | 6/1996 | Edmond et al. | 257/77 |
| 5,622,180 | 4/1997 | Tammi et al. | 600/390 |

FOREIGN PATENT DOCUMENTS

| | | |
|---|---|---|
| B-19 09 882 | 9/1970 | Germany . |
| A-28 05 202 | 8/1978 | Germany . |
| 57-74009 | 10/1980 | Japan . |
| A-2 052 050 | 1/1981 | United Kingdom . |

OTHER PUBLICATIONS

Hecht, "Optics," Second Addition, Addison–Wesley Publishing Co., Massachusetts, p. 72, 1987.

Powers, "An Intro. to Fiber Optic Systems," Aksen Publishers, IL, pp. 105–108, 1993.

Hecht, "Optics", Addison–Wesley Publishing Co., Reading, Massachusetts, 1987, p. 72.

*Primary Examiner*—Michael Peffley
*Assistant Examiner*—Bryan K. Yarnell
*Attorney, Agent, or Firm*—Mark P. Watson

[57] ABSTRACT

An organism information measuring method and an arm wear type pulse-wave measuring method having a sensor unit having a size that does not cause any inconvenience to a user when the user is doing an exercise, such as jogging, so that information about an organism, such as the pulse rate, is measured. The arm wear type pulse-wave measuring apparatus has a wrist band for putting the body of the apparatus on the arm; and a sensor unit that is put on the root of a finger by a sensor securing band. If the finger is irradiated with light by a LED in the foregoing state, light reaches the blood vessel and is reflected. The reflected light is received by a phototransistor in such a manner that the quantity of received light corresponds to change in the quantity of blood occurring due to pulse waves of the blood. The LED is of a type capable of emitting blue light and has a light emission wavelength peak of 450 nm. The phototransistor has a light receiving wavelength region in a range from 300 nm to 600 nm.

5 Claims, 11 Drawing Sheets

ORGANISM INFORMATION MEASURING METHOD AND ARM WEAR TYPE PULSE-WAVE MEASURING METHOD

BACKGROUND OF THE INVENTION

1. Field of the Invention

The present invention relates to an organism information measuring apparatus, such as a pulse-wave measuring apparatus, that is capable of displaying information about the pulse wave, such as the pulse rate. More particularly, the present invention relates to an apparatus that irradiates an organism with light and detects light reflected by the organism to measure information about the organism, such as the pulse waves. In particular, the present invention relates to an arm wear type pulse-wave measuring apparatus that is capable of measuring information about the organism during an exercise, such as jogging, running or cycling.

2. Description of the Related Art

Apparatuses for measuring information about an organism, such as pulse waves, include, in the category thereof, electronic apparatuses of a type that optically detects change in the quantity of blood to display information about an organism in accordance with results of the detection. In an optical pulse-wave measuring apparatus (an organism information measuring apparatus) of the foregoing type, a light emitting device, such as an LED (Light Emitting Diode), irradiates the fingertip or the like with light, and light reflected by the organism (the blood vessel) is received by a light receiving device, such as a phototransistor so that change in the quantity of blood occurring due to the pulse waves of the blood is detected as change in the quantity of the received light. In response to a pulse wave signal obtained from the detection, change in the pulse rate or the pulse waves are displayed. As the light to be emitted from the light emitting device, infrared rays have been employed. If external light (sunlight or the like) is made incident upon the light receiving device, change in the quantity of the external light causes the quantity of received light to be changed. Therefore, the conventional pulse-wave measuring apparatus has a light shielding cover to cover the portion to be detected, such as the fingertip, so that influence of the external light is prevented.

However, if the conventional pulse-wave measuring apparatus has a large light shielding cover, use of the apparatus in a place, such as outdoors, that is irradiated with external light results in that a portion of the external light passes through the finger and reaches the light receiving device. Thus, the conventional pulse-wave measuring apparatus has a problem in that the change in the illuminance of external light causes pulse waves to be detected erroneously. Therefore, the conventional pulse-wave measuring apparatus encounters a limitation in that it can be used only in a place that is not irradiated with external light or a place in which the constant illuminance of external light can be attained. To eliminate the foregoing limitation, a larger-scale light shielding structure must be provided to prevent influence of external light. Therefore, the size of the pulse-wave measuring apparatus cannot be reduced, and therefore the conventional pulse-wave measuring apparatus cannot be used as an apparatus that is able to measure information about pulse waves during exercise, such as jogging, running or cycling.

To overcome the foregoing problem, a pulse-wave sensor has been disclosed in Japanese Utility-Model Laid-Open No. 57-74009 which, in addition to the device for detecting pulse waves, comprises an external-light detection device for detecting external light and which compensates influence of external light in accordance with results of the detection of external light obtained by the external-light detection device. However, provision of the external-light detection device and a compensation circuit for the pulse waves sensor prevents size and cost reductions. As described above, any of the conventional countermeasures against external light has been unsatisfactory in view of practical use.

Furthermore, as a pulse-wave measuring apparatus of the foregoing type, there has been a desire for an arm wear type apparatus that is capable of measuring the pulse rate and the like during jogging, running, cycling or a marathon race. To constitute a pulse-wave measuring apparatus of the foregoing type, a small size sensor unit is required which can be put on the root of the finger. If a small sensor is put on the root of the finger, the user is able to lightly clench the fist.

In view of the foregoing, the inventors of the present invention have performed a variety of investigations for the reason why pulse waves are erroneously detected due to change in the illuminance of external light. As a result, it is concluded that infrared rays for use in the detection system of the conventional pulse-wave measuring apparatus have an excessively large transmittance with respect to the organism that causes external light to easily reach the light receiving device through the organism even if a light shielding cover is provided. Thus, if the foregoing problem can be overcome, a practical countermeasure against external light can be provided.

SUMMARY OF THE INVENTION

Accordingly, an object of the present invention is to realize an organism information measuring apparatus having an optical system, which is not easily affected by external light, to omit a large-scale light shielding structure and to suspend limitations of conditions for use. Another object of the present invention is to provide an arm wear type pulse-wave measuring apparatus having a sensor unit having a small size that does not obstruct a user to perform exercise, such as jogging, so as to be capable of measuring information about pulse waves, such as the pulse rate.

In order to overcome the foregoing objects, an organism information measuring apparatus according to the present invention comprises: a light emitting portion for irradiating a portion of an organism with light; a detection portion having a light receiving portion for receiving light emitted by the light emitting portion and reflected by the organism; and an organism information display portion for displaying information about the organism in accordance with results of detection obtained by the detection portion, wherein the information about the organism is displayed in accordance with results of detection in a wavelength region from about 300 nm to about 700 nm obtained by the detection portion.

When the detection in the foregoing wavelength region is performed, it is preferable that the light emitting portion has a light emitting wavelength region at least in a range from about 300 nm to about 700 nm, and assuming that a light receiving wavelength region of the light receiving portion is $\lambda$ nm, the light receiving wavelength region is in a range that satisfies the following expression:

$$0 < \lambda \leq 700.$$

An organism information measuring apparatus of the foregoing type is able to form a pulse-wave measuring apparatus in which information about pulse waves is, as the information about an organism, displayed in accordance with the results of detection obtained by the detection portion.

An arm wear type pulse-wave measuring apparatus according to the present invention comprises: a sensor unit having a light emitting portion for irradiating the surface of a finger with light, a light receiving portion capable of receiving light emitted by the light emitting portion and reflected by the finger, and a sensor securing band for securing the sensor unit on the finger in a manner such that a light receiving surface of the light receiving portion and a light emitting surface of the light emitting portion face the surface of the finger; a pulse-wave measuring apparatus having a display portion for displaying information about pulse waves obtained in accordance with results of detection performed by the light receiving portion; a wrist band for putting the pulse-wave measuring apparatus on the arm; a cable which extends from the sensor unit and through which the result of detection performed by the light receiving portion is input to the pulse-wave measuring apparatus, wherein the information about pulse waves is displayed in accordance with results of detection in a wavelength region from about 300 nm to about 700 nm performed by the light receiving portion.

The sensor unit can be put on the region from the root of the finger to the joint of the finger so that a user is able to lightly clench the fist if the sensor unit is put on the finger.

It is preferable that an InGaN type (Indium-Gallium-Nitrogen type) blue LED be employed as the light emitting portion, and a GaAsP type (Gallium-Arsenic-phosphorus type) phototransistor be employed as the light receiving portion.

In the arm wear type pulse-wave measuring apparatus (organism information measuring apparatus) according to the present invention, a finger or the wrist is irradiated with light emitted by the light emitting portion, such as the LED; light reflected from the blood vessel is detected by the light receiving portion, such as the phototransistor, so that change in the quantity of blood occurring due to pulse waves of the blood is detected as the change in the quantity of received light; and change in the pulse rate or the pulse waves is displayed in accordance with the pulse wave signal obtained due to the detection.

The information about an organism is displayed in accordance with the results of detection in the wavelength region from 300 nm to 700 nm obtained by the detection means. Light included in external light that has the wavelength region of 700 nm or shorter does not reach the light receiving portion through the finger serving as the photoconductor. On the other hand, light in the region of the wavelength shorter than 300 nm is substantially completely absorbed by the surface of the skin. The arm wear type pulse-wave measuring apparatus according to the present invention performs detection in the foregoing wavelength region by making the wavelength region of the light emitting portion to be in a range from, for example, 300 nm to 700 nm and that of the light receiving portion to be 700 nm or shorter. As a result, the results of the detection are not affected by external light so that information about an organism is measured from the results of the detection in the wavelength region from 300 nm to 700 nm according to only light from the light emitting portion. Therefore, erroneous detection of pulse waves due to external light can be prevented so far as external light is not directly made incident upon the detection portion. Thus, a large-scale light shielding structure is not required.

As a result, even if a small sensor unit, that can be put on a portion from the root to the joint of the thumb, the middle finger, the ring finger or the little finger, is used, external light can satisfactorily be shielded. If the foregoing small sensor unit is used, it does not cover the finger when it is put on the root of the finger, whereby allowing a user to lightly clench the fist. Thus, no problem arises during exercise, such as jogging, running or cycling.

Hemoglobin in the blood has a light absorption factor with respect to light having a wavelength region in a range from 300 nm to 700 nm which is considerably larger than the light absorption factor with respect to infrared rays. When an organism is irradiated with light having the wavelength region in the range from 300 nm to 700 nm to be adaptable to the light absorption characteristics of hemoglobin, the intensity of light reflected by the organism (the blood vessel) is considerably changed to follow the change in the quantity of the blood. Therefore, the S/N ratio of the pulse wave signal can be raised.

As a result of measurement of the distribution of body temperature from the palm to the fingertip, the temperature of the fingertip is considerably lowered when the ambient temperature is low. On the other hand, the temperature of the root of the finger cannot relatively be lowered. That is, the bloodstream at the root of the finger is not reduced excessively even in a cold day. Therefore, putting the sensor unit at the root of the finger enables information about an organism, such as the pulse rate, to be accurately measured if a user performs exercise outdoors, such as running. The method according to the present invention is an excellent measuring method that cannot be obtained by a so-called finger acuminate pulse wave measuring method that is a conventional method for measuring the bloodstream at the fingertip.

Other objects and attainments together with a fuller understanding of the invention will become apparent and appreciated by referring to the following description and claims taken in conjunction with the accompanying drawings.

BRIEF DESCRIPTION OF THE DRAWINGS

FIG. 2(*b*) is an explanatory view showing that a sensor securing band of the sensor unit (the detection unit) for use in the arm wear type pulse-wave measuring apparatus is developed;

FIG. 2(*c*) is an explanatory view showing the structure of another sensor unit (a detection unit);

FIG. 12($b$) is an explanatory graph showing the relationship between the wavelength of light and the light absorption factors of various hemoglobin;

DESCRIPTION OF THE PREFERRED EMBODIMENTS

Overall Structure

Figure 1:
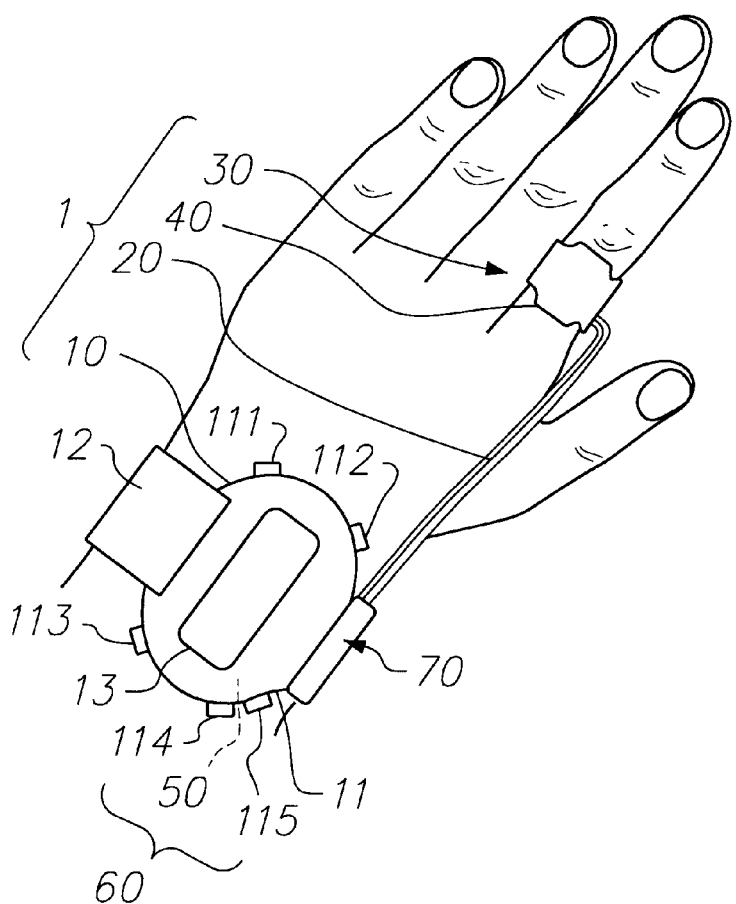
FIG. 1 is an explanatory view showing that an arm wear type pulse-wave measuring apparatus (an organism information measuring apparatus) according to an embodiment of the present invention is used.
Figure 1A:
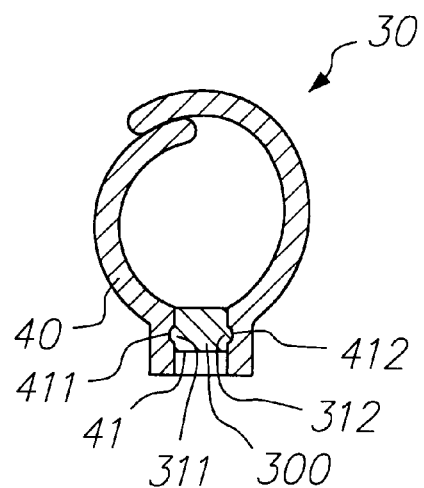
FIG. 1A is a cross sectional view of the sensor unit of the measuring apparatus shown in FIG. 1.
Figure 2A:
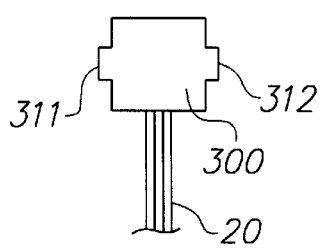
FIG. 2(*a*) is a plan view of an optical unit of a sensor unit (a detection unit) for use in the arm wear type pulse-wave measuring apparatus shown in FIG. 1.
Figure 2B:
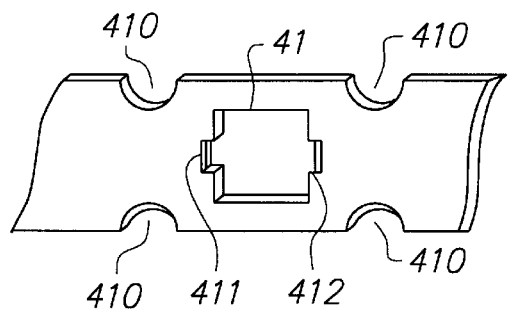
Figure 2C:
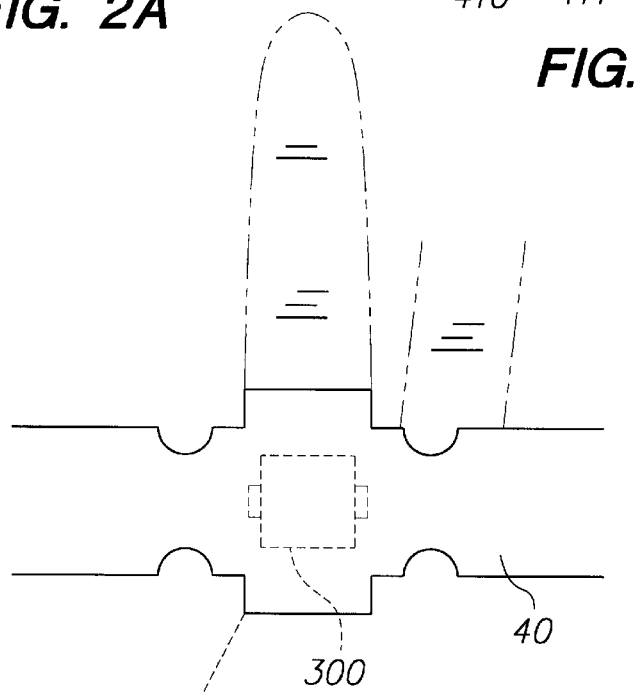
Figure 3:
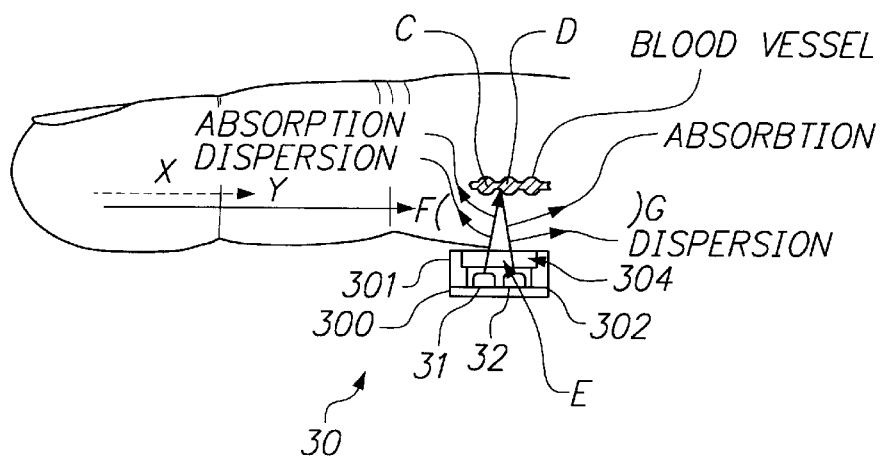
FIG. 3 is an explanatory view showing that the sensor unit of the arm wear type pulse-wave measuring apparatus shown in FIG. 1 put on the root of the finger and the operation of the same.

FIG. 1 is a view of explanatory showing that an arm wear type pulse-wave measuring apparatus according to this embodiment is being used. FIG. 2 ($a$) is a plan view of an optical unit of a sensor unit (a detection unit) employed in the foregoing arm wear type pulse-wave measuring apparatus. FIG. 2 ($b$) is a view of explanatory showing a state where a sensor securing band for the sensor unit (the detection unit) employed in the arm wear type pulse-wave measuring apparatus is developed. FIG. 2($c$) is a view of explanatory showing the structure of another sensor unit (a detection unit). FIG. 3 is a view of explanatory showing that the sensor unit (the detection unit) put on the root of the finger and as well as showing the operation of the sensor unit.

In FIG. 1, the arm wear type pulse-wave measuring apparatus 1 (an organism information measuring apparatus) according to this embodiment comprises an apparatus body 10 (a body of the pulse-wave measuring apparatus 1) having the structure of a wristwatch; a cable 20 (a signal transmission portion) connected to the apparatus body 10; and a sensor unit 30 disposed at the leading end of the cable 20. The apparatus body 10 is made detachable with respect to the arm by means of a wrist band 12. The sensor unit 30 has a sensor securing band 40 that is about 15 mm in width. The sensor securing band 40 enables the sensor unit 30 to be put on the root of the finger. Since the cable 20 extending from the sensor unit 30 is provided with a connector portion 70 with which switching can be performed between a state where the cable 20 is connected to the apparatus body 10 and a state where the same is removed from the apparatus body 10, removal of the sensor unit 30 and the cable 20 from the apparatus body 10 enables the arm wear type pulse-wave measuring apparatus 1 to be as well as used as a usual wristwatch.

Structure of Apparatus Body

The apparatus body 10 comprises a watch case 11 including a time measuring function portion. The watch case 11 has, on the upper surface thereof, a liquid crystal display unit 13 (a display portion) for displaying, in addition to the present time and date, information about pulse waves (information about the organism) in accordance with results of detection obtained by the sensor unit 30. The watch case 11 includes a data processing circuit 50 for processing, for example, a detection signal to display change in the pulse rate or and the like in accordance with the results of the detection obtained by the sensor unit 30. The data processing circuit 50 and the liquid crystal display unit 13 form an organism information display portion 60. Note that the watch case 11 has, on the outer surface thereof, button switches 111, 112, 113, 114 and 115 for adjusting time and switching the display mode.

Electric power is supplied to the arm wear type pulse-wave measuring apparatus 1 from a battery (not shown) included in the watch case 11. The cable 20 is used to supply electric power from the battery to the sensor unit 30 and to input the results of the detection obtained by the sensor unit 30 to the data processing circuit 50.

Structure of Sensor Unit

The sensor unit 30 comprises the sensor securing band 40 and an optical unit 300. The sensor securing band 40 is made of a resin molded member having a thickness which permits flexibility so that the sensor securing band 40 is curled up in a usual state. The sensor securing band 40 is spread in the foregoing state, followed by being wound around the root of the finger. Removal of the hand in the foregoing state causes the sensor securing band 40 to be wound around the root of the finger due to the shape restoring force thereof.

The sensor securing band 40 has a thick portion at substantially the central portion thereof, the thick portion having a hole 41 that is capable of accommodating the optical unit 300.

As shown in FIG. 2($a$), the optical unit 300 is, with resin, molded into a rectangular shape having a pair of projection portions 311 and 312 on the two sides thereof. The cable 20 is extended from the inside portion of the optical unit 300.

On the other hand, as shown in FIG. 2($b$), the hole 41 of the sensor securing band 40 has the shape and size which permit accommodation of the optical unit 300 therein. The hole 41 has concavities 411 and 412 for receiving the projections 311 and 312 when the optical unit 300 is placed in the hole 41 so that undesirable separation is prevented. The sensor securing band 40 has four narrow portions 410 for easily putting the sensor securing band 40 on the finger.

In view of the sensor unit 30 being required to enable the fist to be clenched lightly in a state where the same is put on the root of the finger, the width of the sensor securing band 40 may be about 20 mm to 25 mm. As shown in FIG. 2(c), a structure may be employed in which only a portion of the sensor securing band 40, to which the optical unit 300 is attached, is widened.

As the sensor securing member, that is typified by the sensor securing band 40, it may be in the form of a ring-like shape that is put on the finger, as well as in the form of the band type shape that is wound around the finger. An example of the sensor securing member has a hollow and cylindrical shape made of fiber, such as rubber, having strechability and holding member. The foregoing member has a structure, in which the sensor unit 30 is enclosed in the ring-like shape, in place of the band-like structure according to this embodiment. Therefore, the foregoing sensor securing member is put on the finger in such a manner that it is received by the leading end of the finger, followed by being moved to the root of the finger in place of a manner that it is wound around the finger.

As the method of securing the sensor unit 30, either of the foregoing sensor securing members may be employed. The hole 41 according to this embodiment so formed in the sensor securing band 40 as to accommodate the sensor unit 30 may be omitted from the structure. That is, the sensor securing member and the sensor unit 30 have independent shapes in the foregoing case. In the foregoing case, the sensor unit 30 is held by the hand when the sensor securing band 40 is wound around the finger. By employing the foregoing method, the shape of the sensor securing band 40 and that of the sensor unit 30 can be simplified so that advantages are obtained in that the manufacturing process can be performed easily and that the cost can be reduced.

Structure of Optical Unit

In this embodiment, as shown in FIG. 3, an LED 31 irradiates the finger with light, and light reflected by the organism (the blood vessel) is received by a phototransistor 32 so as to detect pulse waves from the organism (the blood vessel).

Referring to FIG. 3, the optical unit 300 has the outer shape formed by a sensor frame 301 serving as the case body, a reverse cover 302 and a glass plate 304, and a circuit board 305 opposing the glass plate 304.

Figure 4:
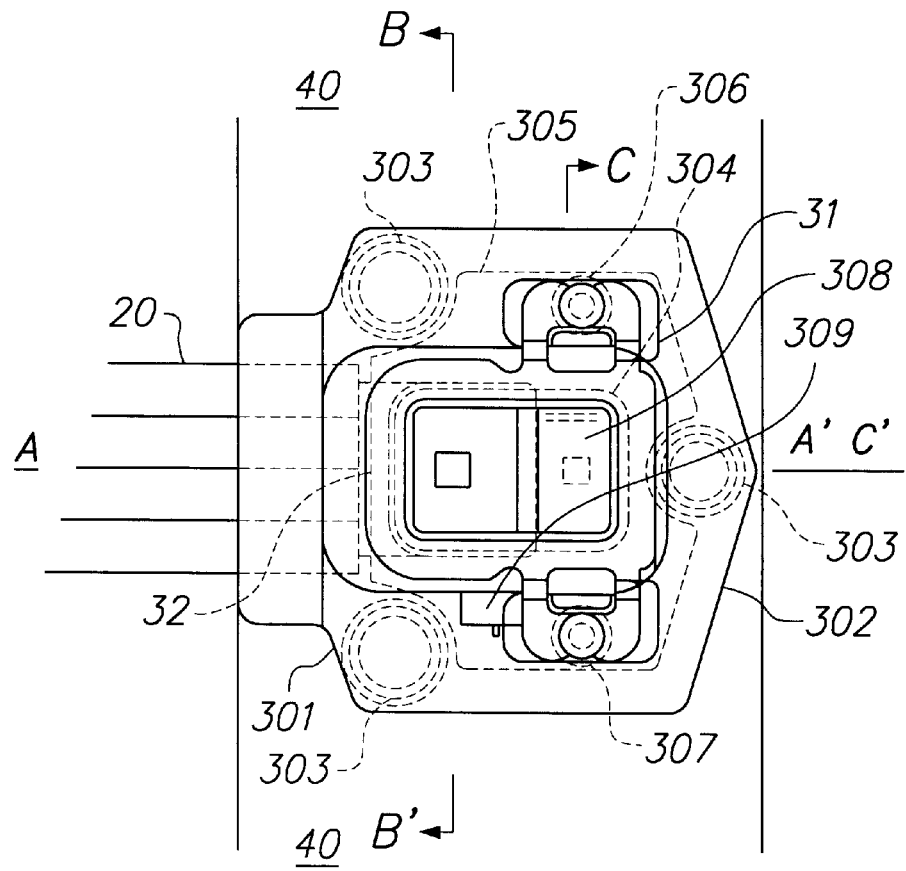
FIG. 4 is a plan view showing the structure of the detection unit (the optical unit) of the arm wear type pulse-wave measuring apparatus shown in FIG. 1.
Figure 5:
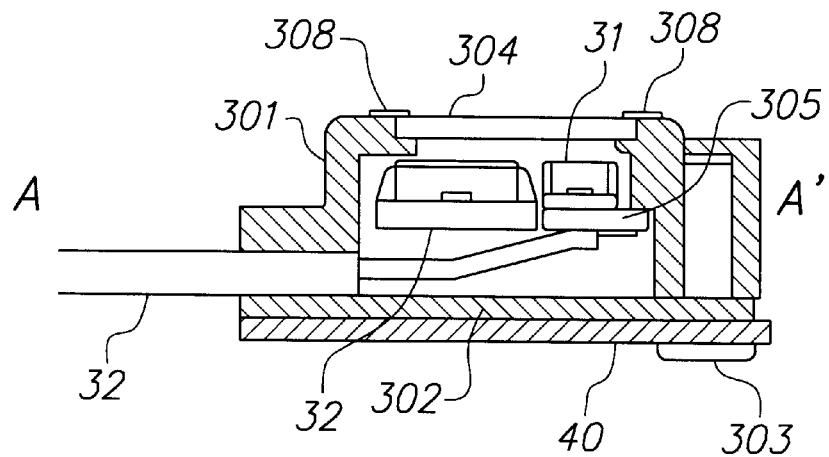
FIG. 5 is a cross sectional view taken along line A–A' of FIG. 4.
Figure 6:
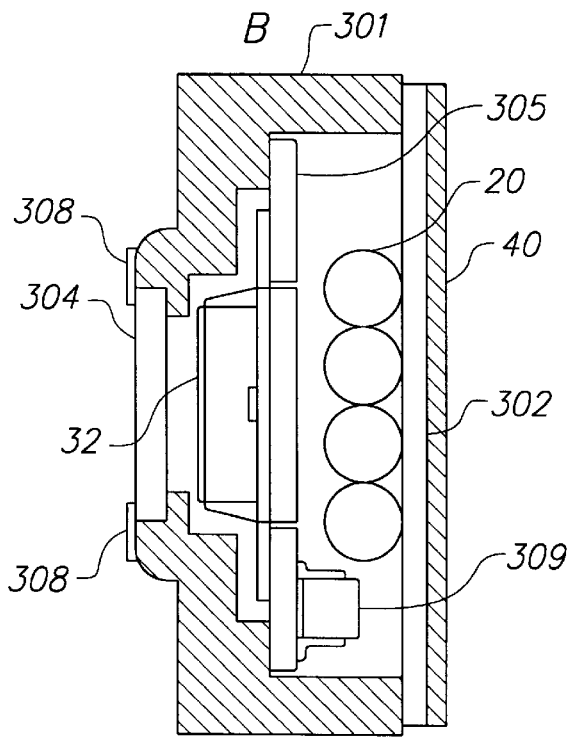
FIG. 6 is a cross sectional view taken along line B–B' of FIG. 4.
Figure 7:
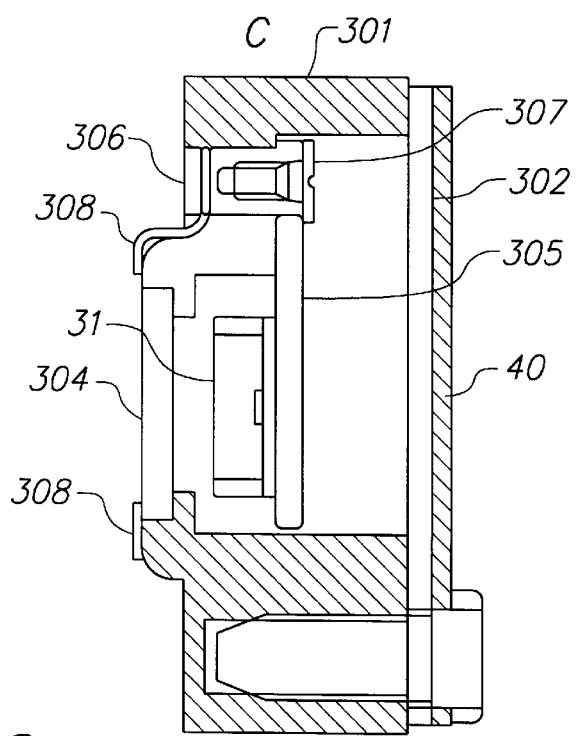
FIG. 7 is a cross sectional view taken along line C–C' of FIG. 4.

Referring to FIGS. 4 to 7, the structure of the optical unit 300 will now be described in detail. FIG. 4 is a plan view of the optical unit 300, FIG. 5 is a cross sectional view taken along line A–A' of FIG. 4, FIG. 6 is a cross sectional view taken along line B–B' of FIG. 4, and FIG. 7 is a cross sectional view taken along line C–C' of FIG. 4.

As shown in the foregoing figures, the reverse cover 302 is mounted on the sensor frame 301 serving as the case body of the optical unit 300 so that the internal portion serves as a space for accommodating elements. The reverse cover 302 is secured to the sensor frame 301 with three reverse-cover securing screws 303. The reverse-cover securing screws 303 secure the sensor securing band 40 to the lower surface of the reverse cover 302, while the sensor securing band 40 extends from the optical unit 300 into the two side directions. The cable 20 is extended from the inside portion of the sensor frame 301 in a direction perpendicular to the sensor securing band 40. The glass plate 304 having a function to serve as an optical filter forms a light transmissive window on the upper surface of the sensor frame 301. The circuit board 305 is so secured in the sensor frame 301 as to oppose the glass plate 304.

Electronic parts, such as an LED 31, a phototransistor 32 (a sensor unit having a filter), a transistor 309, resistors and capacitors (not shown), are mounted on the circuit board 305. The light emitting surface and the light receiving surface of the corresponding LED 31 and the phototransistor 32 are caused to face the glass plate 304. Note that the circuit board 305 is secured to the sensor frame 301 in such a manner that circuit-board securing threads 307 are fastened by two pins 306 inserted from the upper surface of the sensor frame 301. Also an earth plate 308 is secured by the pins 306.

Figure 8:
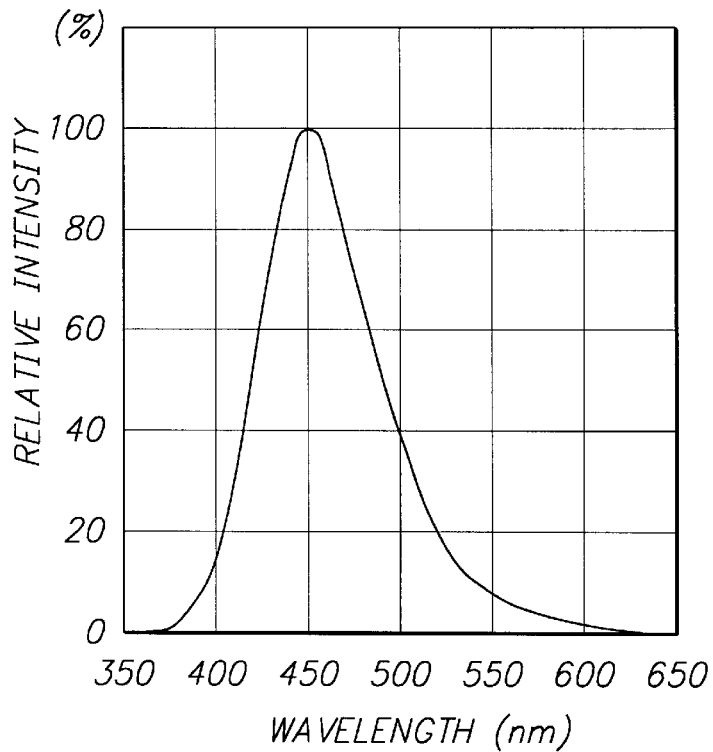
FIG. 8 is an explanatory graph showing the light emission spectrum of an InGaN type blue LED for use in the arm wear type pulse-wave measuring apparatus shown in FIG. 1.

This embodiment is characterized in that a blue LED made of InGaN (Indium-Gallium-Nitrogen type) material is employed to serve as the LED 31. The emission spectrum of the LED 31 has the emission peak at 450 nm as shown in FIG. 8, while the emission wavelength region of the same is ranged from 350 nm to 600 nm.

Figure 10:
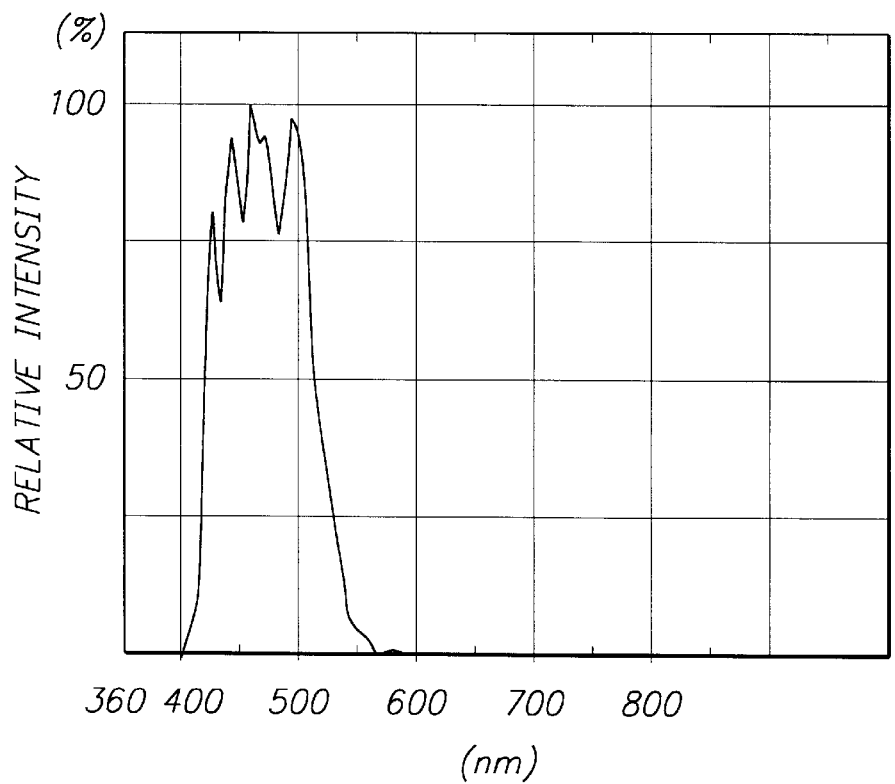
FIG. 10 is an explanatory graph showing the light receiving characteristics of a phototransistor unit having an optical filter for use in the arm wear type pulse-wave measuring apparatus shown in FIG. 1.
Figure 9:
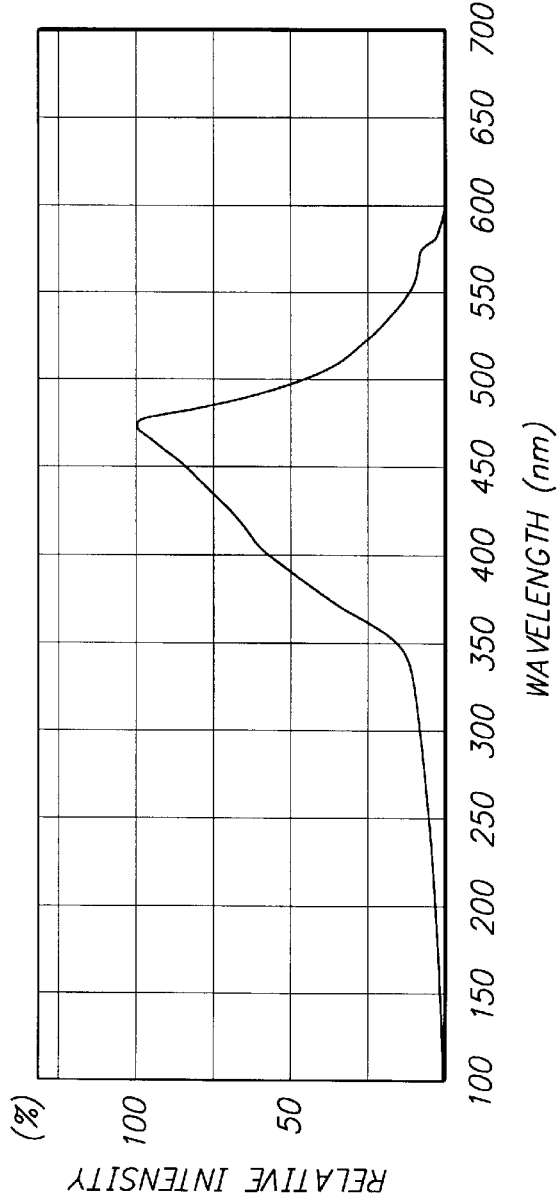
FIG. 9 is an explanatory graph showing the light receiving characteristics of the InGaP type phototransistor for use in the arm wear type pulse-wave measuring apparatus shown in FIG. 1.

To be adaptable to the LED 31 having the foregoing light emission characteristics, a GaAsP (Gallium-Arsenic-phosphorus type) phototransistor is employed as the phototransistor 32. The light receiving wavelength region of the phototransistor 32 is, as shown in FIG. 9, such that the main sensitive region is in a range from 300 nm to 600 nm and also a sensitive region exists in a region lower than 300 nm. As the phototransistor 32, a sensor unit of a type having an optical filter attached to the device is sometimes employed. An example of the light receiving wavelength region of the sensor unit above is, as shown in FIG. 10, such that the main sensitive region is in a range from 400 nm to 550 nm. Since the foregoing LED 31 and the phototransistor 32 consume relatively small electric power, a long operation time can be realized even if one small-size battery is used to operate, for example, the arm wear type pulse-wave measuring apparatus 1 according to the present invention having the time measuring function and the pulse wave measuring function.

Structure of Data Processing Circuit

Figure 11:
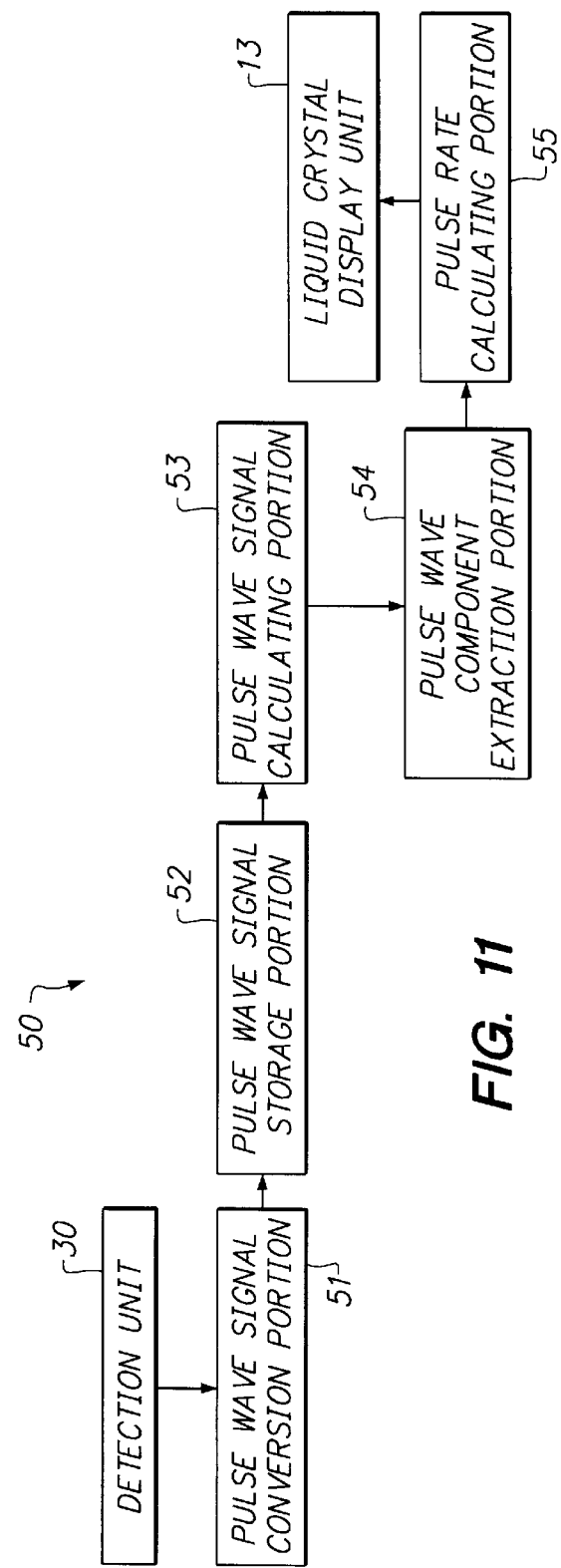
FIG. 11 is a block diagram showing the structure of a data processing circuit of the arm wear type pulse-wave measuring apparatus shown in FIG. 1.

Referring to FIG. 11, the structure of the data processing circuit 50 disposed in the watch case 11 will now be described. FIG. 11 is a block diagram showing the structure of the data processing circuit 50.

In the data processing circuit 50, a pulse-wave signal conversion portion 51 converts a signal supplied from the sensor unit 30 through the cable 20 into a digital signal to transmit the digital signal to a pulse-wave storage portion 52. The pulse-wave storage portion 52 is a RAM for storing pulse wave data converted into the digital signal. A pulse-wave signal calculating portion 53 reads the signal stored in the pulse-wave storage portion 52 to analyze the frequency of the signal so as to transmit results of the analysis to a pulse-wave component extraction portion 54. The pulse-wave component extraction portion 54 extracts the pulse wave component from the signal supplied from the pulse-wave signal calculating portion 53 to transmit the extracted component to a pulse-rate calculating portion 55. The pulse-rate calculating portion 55 calculates the pulse rate in accordance with the frequency component of the supplied pulse waves to transmit results of the calculation to the liquid crystal display unit 13.

Operation

The operation of the thus-constituted arm wear type pulse-wave measuring apparatus 1 will now be described briefly with reference to FIGS. 1, 3 and 11.

Referring to FIG. 1, when the arm wear type pulse-wave measuring apparatus 1 is used as a usual wristwatch, the apparatus body 10 is put on the arm by means of the wrist band 12 in a state where the cable 20 and the sensor unit 30 are removed from the connector portion 70 of the apparatus body 10.

In a case where the arm wear type pulse-wave measuring apparatus 1 is used to measure information about pulse waves, such as the pulse rate, during exercise, such as jogging or running, the cable 20 is connected to the connector portion 70 of the apparatus body 10, and then the apparatus body 10 is put on the arm by means of the wrist band 12. After the sensor unit 30 (the glass plate 304 of the optical unit 300) has been brought into close contact with the finger by the sensor securing band 40, exercise, such as jogging or running, is performed.

In the foregoing state, when the LED 31 emits light to the finger as schematically shown in FIG. 3, light reaches the blood vessel, and a portion of light is absorbed by the hemoglobin in the blood. Another portion of light is reflected by the hemoglobin. Light reflected by the finger (the blood vessel) is received by the phototransistor 32; thus the change in the quantity of received light corresponds to change in the quantity of blood occurring due to pulse waves of the blood. That is, if the quantity of blood is large, the reflected light is weakened. If the quantity of blood is small, the reflected light is strengthened. Therefore, observation of the change in the intensity of the reflected light performed by the phototransistor 32 enables the pulse waves or the like to be detected. To perform the foregoing detection, the data processing circuit 50 shown in FIG. 11 converts the signal supplied from the phototransistor 32 (the sensor unit 30) into a digital signal to analyze the frequency of the digital signal to calculate the pulse rate. The pulse rate obtained due to the calculation is displayed on the liquid crystal display unit 13. That is, the arm wear type pulse-wave measuring apparatus 1 serves as a pulsemeter.

Referring back to FIG. 3, a portion of light emitted by the LED 31 is allowed to pass through the finger to reach the blood vessel as indicated by an arrow C. Thus, reflected light from the hemoglobin in the blood reaches the phototransistor 32, as indicated by an arrow D. The quantity of light received through the foregoing route is the quantity of light reflected by the organism. A portion of light emitted by the LED 31 is reflected by the surface of the finger as indicated by an arrow E to reach the phototransistor 32. The quantity of light received through the foregoing route is the quantity of light reflected by the skin. A portion of light emitted by the LED 31 and that reflected by the blood vessel are absorbed or dispersed in the finger, as indicated by arrows F and G, so that the portions of the light do not reach the phototransistor 32.

To detect the pulse waves, results of detection performed in the wavelength region from 350 nm to 600 nm is, in this embodiment, used in place of infrared rays as have been employed in the conventional structure to display information about an organism. That is, the sensor unit 30 comprises the LED 31, the light emission wavelength region of which is in the range from 350 nm to 600 nm; and the phototransistor 32, the main light receiving wavelength region of which is in the range from 300 nm to 600 nm. In accordance with results of detection in the wavelength region from 350 nm to 600 nm, in which the foregoing two regions overlap, information about the organism is displayed. By using the foregoing sensor unit 30, light included in external light, the wavelength region of which is shorter than 700 nm, does not reach the phototransistor 32 (the light receiving portion) through the finger serving as a phototransistor, as described later. On the other hand, light, the wavelength of which is shorter than 300 nm, is substantially absorbed by the surface of the skin. Therefore, the results of the detection are not affected by external light. Thus, in accordance with the results of the detection in the wavelength region from 300 nm to 700 nm obtained due to only light from the light emitting portion, information about an organism can be measured.

In view of obtaining information about pulse waves without influence of external light, the LED 31 may be an LED having the light emission wavelength region of 300 nm to 700 nm and the phototransistor 32 may be a phototransistor having the light receiving wavelength region of 700 nm or shorter.

Effect of the Embodiment

As described above, the arm wear type pulse-wave measuring apparatus 1 according to this embodiment comprises the LED 31 having the light emission wavelength region of 350 nm to 600 nm; and the phototransistor 32 having the main sensitive region of the light receiving wavelength region of 300 nm to 600 nm. When the phototransistor 32 is a unit formed by combining the device and the filter, the light receiving wavelength region is in a range from 400 nm to 550 nm. Therefore, if the pulse waves are measured in the simple light shielding state shown in FIG. 1, light included in external light that has the wavelength region of 700 nm or shorter does not reach the phototransistor 32 (the light receiving portion) through the finger serving as the photoconductor. Only light having the wavelength region that does not affect the detection passes through the finger serving as the photoconductor. Therefore, in this embodiment, if the exposed portion of the finger is irradiated with external light, results of detection of pulse waves are not affected by external light. As a result, the sensor unit 30 having the detection portion that is light-shielded by the narrow sensor securing band 40 can be employed. Thus, the small sensor unit 30 according to this embodiment enables the user to lightly clench the fist with the same put on the root of the finger thereof so that no problem arises during exercise, such as jogging, running or cycling. Since the cable 20 can be shortened if the sensor unit 30 is put on the root of the finger, the cable 20 is not obstructive during exercise, such as jogging. Therefore, the arm wear type pulse-wave measuring apparatus 1 according to this embodiment is suitable to measure the pulse rate during exercise, such as jogging.

When the distribution of temperature from the palm to the fingertip, the temperature of the fingertip is lowered considerably when the ambient temperature is low and the temperature of the root of the finger cannot easily be lowered. That is, the bloodstream is not lowered considerably at the root of the finger. Thus, if the sensor unit is put on the root of the finger, the information about an organism, such as the pulse rate, can accurately be measured if the user performs exercise outdoors, such as running, in a cold day.

Since the information about pulse waves is obtained by using light having the wavelength region from about 300 nm to about 700 nm, the S/N ratio of the pulse wave signal in accordance with the change in the quantity of the blood is high. The reason for this will now be described.

Figure 12A:
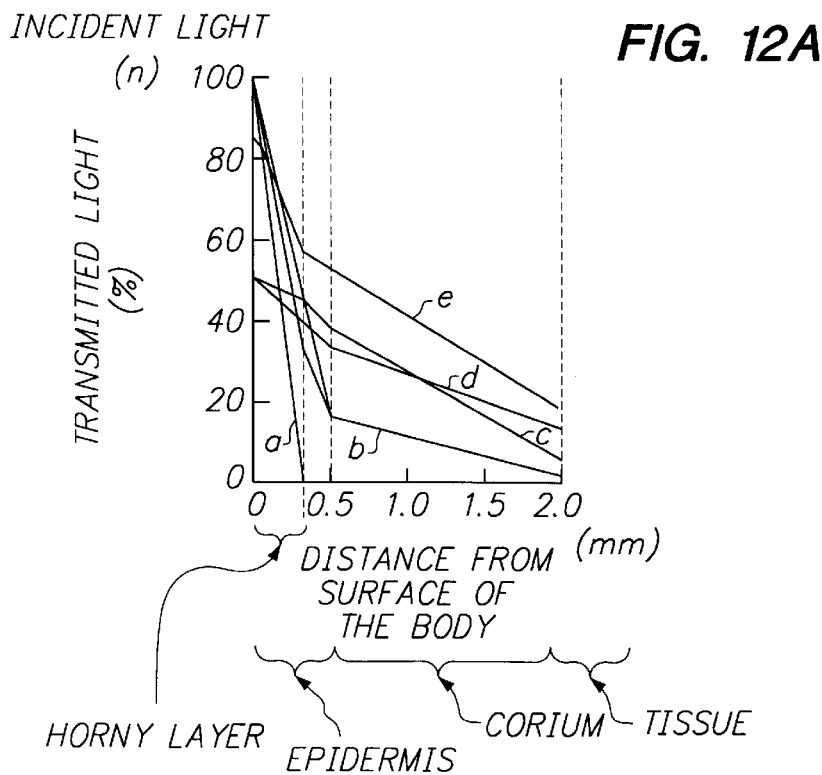
FIG. 12($a$) is a graph showing the relationship between the wavelength of light and light transmittance of the skin.

First, the reason why the influence of external light can be eliminated satisfactorily will now be described with reference to FIG. 12(a). FIG. 12(a) shows the relationship between the wavelength of light and light transmittance of the skin. Polygonal line a indicates transmission characteristic with respect to light having a wavelength of 200 nm, polygonal line b indicates transmission characteristic with respect to light having a wavelength of 300 nm, polygonal line c indicates transmission characteristic with respect to light having a wavelength of 500 nm, polygonal line d indicates transmission characteristic with respect to light having a wavelength of 700 nm and polygonal line e indicates transmission characteristic with respect to light having a wavelength of 1 $\mu$m. As can be understood from FIG. 12(a), light included in external light that has a wavelength of 700 nm or shorter does not easily penetrate the finger. Therefore, if the portion of the finger that is not covered with the sensor securing band 40 is irradiated with external light, external light does not reach the phototransistor 32 through the finger as indicated by dashed line X shown in FIG. 3. Thus, if light having the wavelength of 700 nm or shorter is used as detection light, influence of external light can be prevented only by covering the minimum range of the finger in place of covering the finger over a large area. As a result, the arm wear type pulse-wave measuring apparatus 1 according to this embodiment can be used outdoors. Since a major portion of light in a wavelength region lower than 300 nm is absorbed in the surface of the skin, the substantial light receiving wavelength region is 300 nm to 700 nm even if the light receiving wavelength region is made to be 700 nm or shorter.

Figure 13:
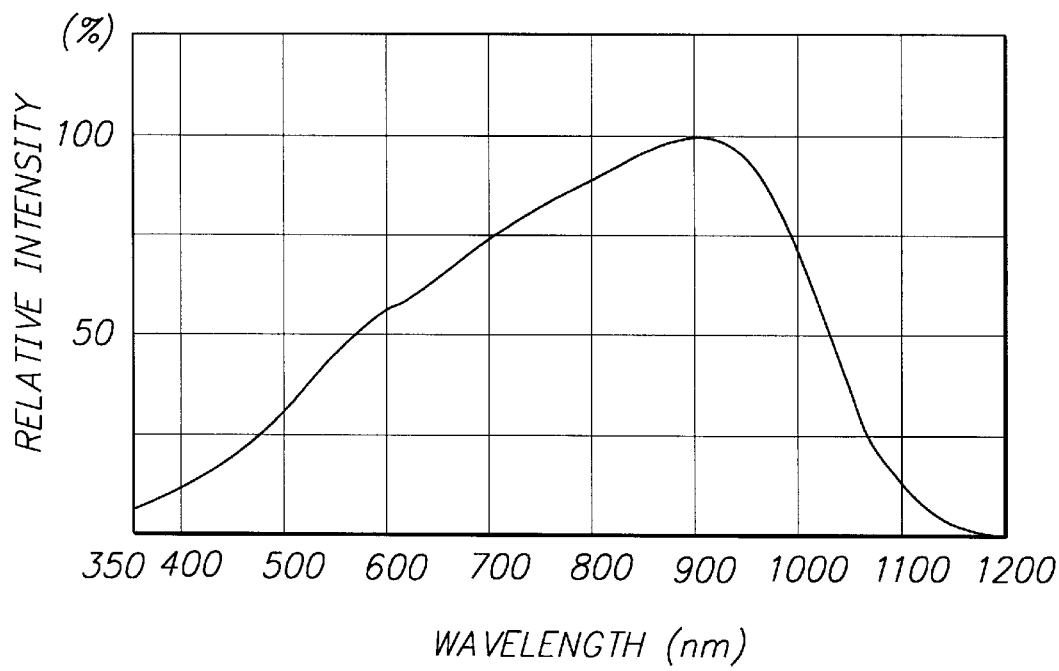
FIG. 13 is an explanatory graph showing the light receiving characteristics of a silicon type phototransistor for use in a conventional pulse-wave measuring apparatus.

On the contrary, if an LED having a light emission peak in a region adjacent to 880 nm, which is in the infrared region, and a silicon type phototransistor are used as have been employed in the conventional structure, the light receiving wavelength region is 350 nm to 1200 nm, as shown in FIG. 13. Therefore, since the conventional optical system (the detection unit) detects pulse waves in accordance with results of detection by means of light included in external light that has a wavelength of 1 $\mu$m that easily reaches the light receiving portion through the finger serving as the photoconductor as indicated by arrow Y shown in FIG. 3, that is, light indicated by polygonal line e of FIG. 12(a), erroneous detection easily takes place due to change in external light.

Figure 12B:
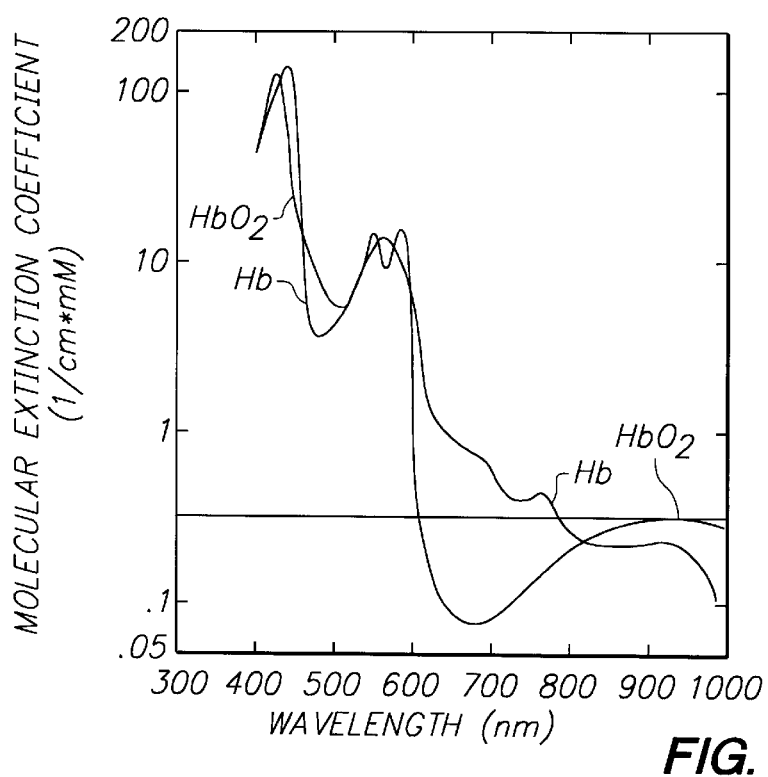

The reason why the pulse-wave measuring apparatus 1 according to this embodiment causes high S/N ratio of the pulse wave signal to be obtained will now be described with reference to FIG. 12(b). FIG. 12(b) is a graph of explanatory showing the relationship between wavelengths of light and light absorption characteristics of a variety of hemoglobin.

FIG. 12(b) shows, with curve Hb, the light absorption characteristics of hemoglobin that has not been bonded with oxygen and light absorption characteristics of hemoglobin that has been bonded with oxygen with curve HbO2. As indicated by the foregoing curves, hemoglobin in the blood has a large light absorption factor with respect to light having a wavelength of 300 nm to 700 nm, the light absorption factor being several times to about 100 times the light absorption factor with respect to light having the wavelength of 880 nm which is the conventional detection light. Therefore, if light having a wavelength region (300 nm to 700 nm) having a large light absorption factor is used as detection light to be adaptable to the light absorption factor of hemoglobin as is employed in this embodiment, the detection values changes in accordance with the change in the quantity of blood with excellent sensitivity attained. Therefore, a high detection ratio (the S/N ratio) of the pulse waves in accordance with change in the quantity of blood can be obtained.

Figure 14A:
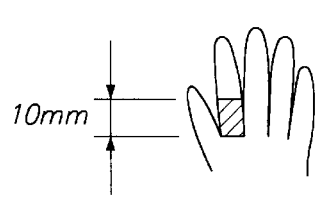
FIGS. 14($a$)–14($e$) are explanatory views showing respective experimental conditions in which the range of the finger, which is shielded from light, is changed to evaluate the degree of introduction of external light into the arm wear type pulse-wave measuring apparatus according to the present invention.
Figure 14B:
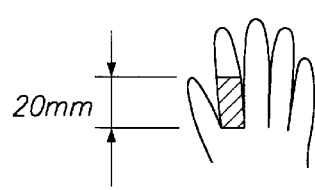
Figure 14C:
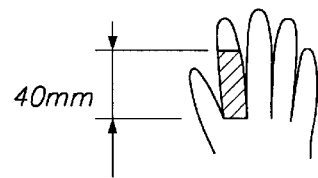
Figure 14D:
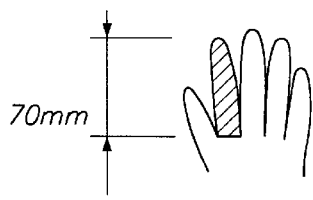
Figure 14E:
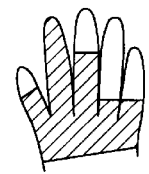

Quantity of Introduced External Light Depending Upon the Light Shielding Condition To evaluate the arm wear type pulse-wave measuring apparatus 1 according to this embodiment, only the quantity of introduced external light was measured in such a manner that the light shielding range with respect to the finger was changed from condition 1 to condition 5 as shown in FIGS. 14(a) to 14(e) so as to be subjected to a comparison with that realized in the conventional pulse-wave measuring apparatus (comparative examples). As the pulse-wave measuring apparatus 1 according to this embodiment, sample 1 comprising the phototransistor 32 having the light receiving sensitivity of 400 nm to 600 nm and sample 2 comprising the phototransistor 32 having the light receiving sensitivity of 300 nm to 700 nm were evaluated. As the comparative examples, samples 3, 4 and 5 were evaluated that had the light receiving sensitivities which were out of 300 nm to 700 nm. Note that condition 1 was a state where the root of the finger was covered with the light shielding cover having a width of 10 mm as shown in FIG. 14 (a), condition 2 was a state where the root of the finger was covered with the light shielding cover having a width of 20 mm as shown in FIG. 14(b), condition 3 was a state where the root of the finger was covered with the light shielding cover having a width of 40 mm as shown in FIG. 14(c), condition 4 was a state where the root of the finger was covered with the light shielding cover having a width of 70 mm as shown in FIG. 14(d), and condition 5 is a state where the overall body of the forefinger, the root of the thumb, the root of the middle finger and portions adjacent to the roots of all fingers were covered with a light shielding cover.

Results of measurement of the quantity of introduced external light under the foregoing conditions were shown in Table 1. The quantities of introduced external light were represented by output currents (unit: $\mu$A) from the phototransistor.

TABLE 1

| Samples | Structure of Sensors According to Examples | | Structure of Sensors According Comparative Examples | | |
| --- | --- | --- | --- | --- | --- |
| | Sample 1 | Sample 2 | Sample 3 | Sample 4 | Sample 5 |
| Light Receiving Region | 400 nm to 600 nm | 300 nm to 700 nm | 300 nm to 1000 nm | 300 nm to 750 nm | 300 nm to 800 nm |
| Light Shielding Conditions | | | | | |
| Condition 1 | 0.006 | 0.008 | 55.3 | 18.3 | 30.4 |
| Condition 2 | 0.005 | 0.007 | 46.4 | 12.2 | 25.2 |
| Condition 3 | 0 | 0.001 | 30.2 | 7.8 | 17.3 |
| Condition 4 | 0 | 0 | 5.1 | 2.2 | 4.4 |
| Condition 5 | 0 | 0 | 0.008 | 0.002 | 0.004 |

As shown in Table 1, the pulse-wave measuring apparatus 1 according to this embodiment (samples 1 and 2) receives light in the wavelength region from 300 nm to 700 nm so that influence of external light can be ignored under any of the foregoing conditions. The reason for this is that light included in external light that has the wavelength region of 700 nm or shorter does not reach the phototransistor 32 (the light receiving portion) through the finger serving as the photoconductor. Therefore, the pulse-wave measuring apparatus 1 according to this embodiment requires the finger to be covered with the sensor unit 30 or the sensor securing band 40 (the light shielding cover) only by a width of 10 mm. On the other hand, the pulse-wave measuring apparatus according to the comparative examples (samples 3, 4 and 5) are able to ignore the influence of external light only in the state (condition 5) where the finger is covered widely such that the overall body of the forefinger, the root of the thumb, the root of the middle finger and portions adjacent to the roots of all fingers were covered with a light shielding cover. Thus, a large-scale light shielding structure is required.

Influence of External Light Depending Upon the Environment

The pulse-wave measuring apparatus 1 according to this embodiment comprising the LED 31 (the blue light source) having the light emission wavelength peak of 450 nm; and the GaAsP type phototransistor 32 having the light receiving wavelength region of 300 nm to 600 nm; and the pulse-wave measuring apparatus (the comparative example) comprising the LED having the light emission wavelength peak of 880 nm and the phototransistor having the light receiving wavelength region of 350 nm to 1200 nm were used to compare and investigate the degree of influence of external light. Results were shown in FIGS. 15 and 16. Data shown in FIGS. 15 and 16 were results of analysis of the frequency to be used as the results of the detection of pulse waves. Among a multiplicity of peaks, peaks each given an arrow correspond to the frequency of the pulse waves.

Figure 15A:
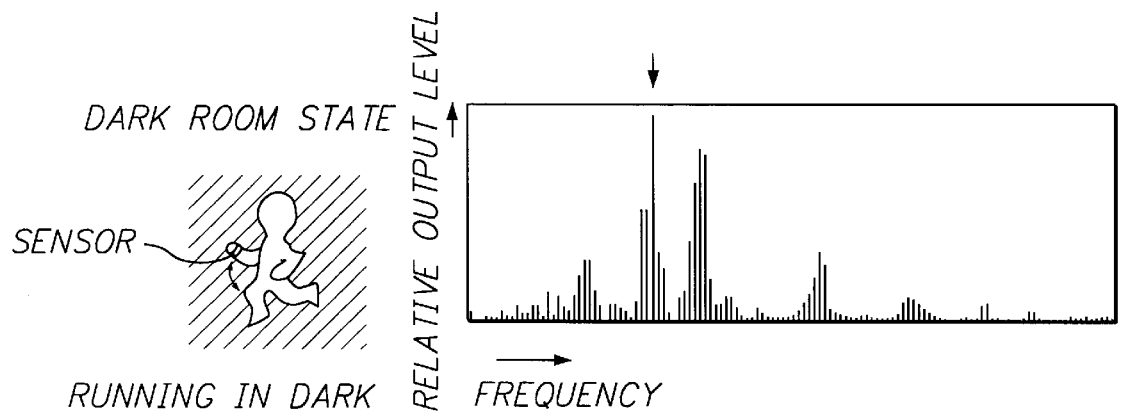
FIGS. 15($a$)–15($c$) are explanatory views showing data of results of analysis of the frequency of results of detection of pulse waves of the pulse-wave measuring apparatus according to the present invention to evaluate influence of external light upon the arm wear type pulse-wave measuring apparatus according to the present invention.
Figure 15B:
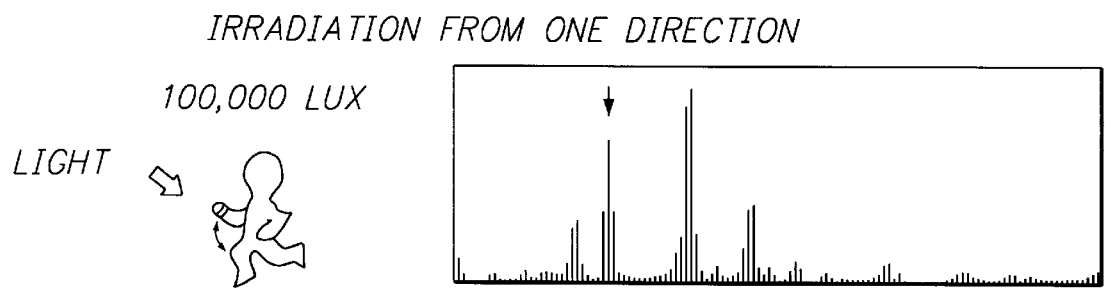
Figure 15C:
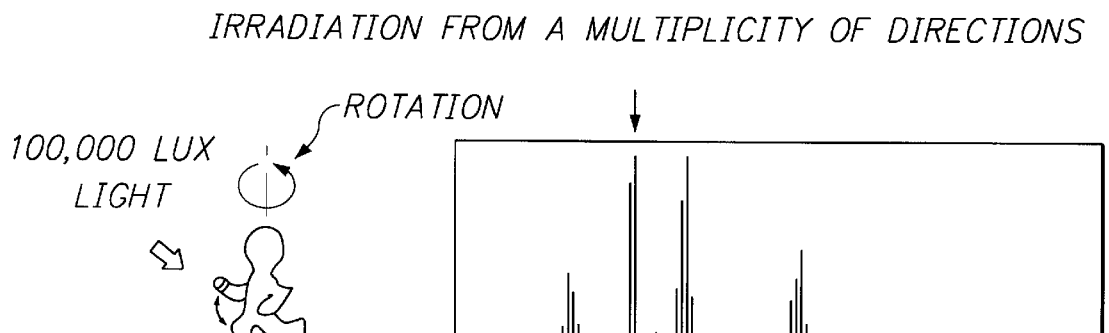

FIG. 15(a) shows results of measurement of pulse waves when a user having the arm wear type pulse-wave measuring apparatus according to this embodiment runs in a dark room. FIG. 15 (b) shows results of measurement of pulse waves when the user having the arm wear type pulse-wave measuring apparatus according to this embodiment runs in a direction toward the sunlight. FIG. 15(c) shows results of measurement of pulse waves when the user having the arm wear type pulse-wave measuring apparatus according to this embodiment so runs circularly that the relative direction of sunlight is varied. In any of the conditions shown in the foregoing figures, the peaks of the pulse waves each of which is given the arrow is clear as compared with other peaks. Thus, it can be understood that the arm wear type pulse-wave measuring apparatus 1 according to this embodiment cannot easily be affected by external light.

Figure 16A:
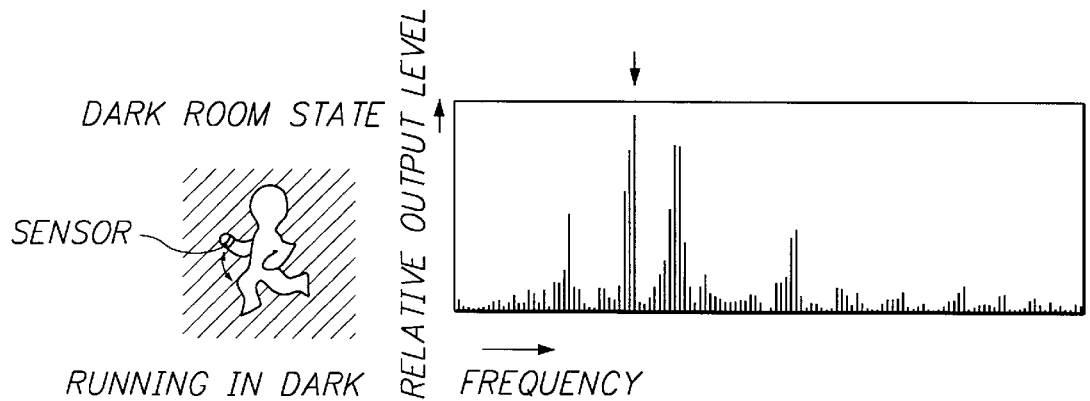
FIGS. 16($a$)–16($c$) are explanatory views showing data of results of analysis of the frequency of results of detection of pulse waves of a pulse-wave measuring apparatus according to a comparative example to evaluate influence of external light upon the arm wear type pulse-wave measuring apparatus according to the present invention.
Figure 16B:
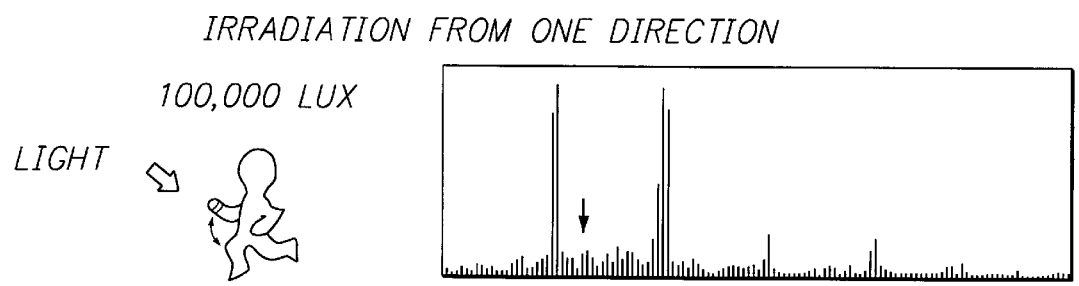
Figure 16C:
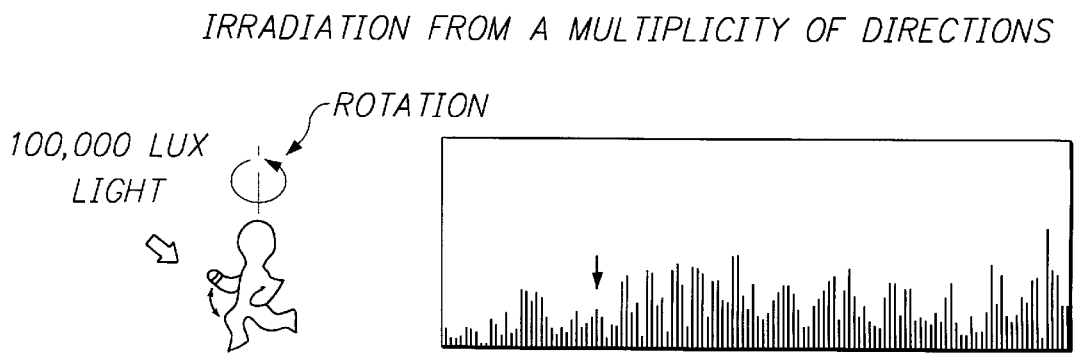

FIG. 16(a) shows results of measurement of pulse waves when the user having the conventional arm wear type pulse-wave measuring apparatus runs in a dark room. FIG. 16(b) shows results of measurement of pulse waves when the user having the conventional arm wear type pulse-wave measuring apparatus runs in a direction toward the sunlight. FIG. 16(c) shows results of measurement of pulse waves when the user having conventional the arm wear type pulse-wave measuring apparatus so runs circularly that the relative direction of sunlight varied. As shown in the figures above, the conventional pulse-wave measuring apparatus is able to measure the pulse waves only in the dark room, and the measurement cannot be performed under condition that external light exists.

Relative Sensitivity of Pulse Wave Signal

Figure 18:
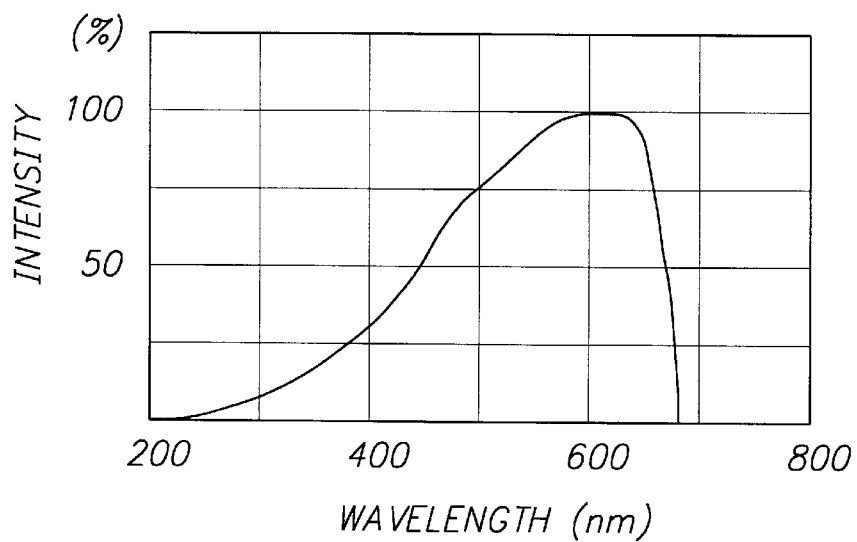
FIG. 18 is an explanatory graph showing light receiving characteristics of a GaAsP type phototransistor for use in the arm wear type pulse-wave measuring apparatus shown in FIG. 1.
Figure 17:
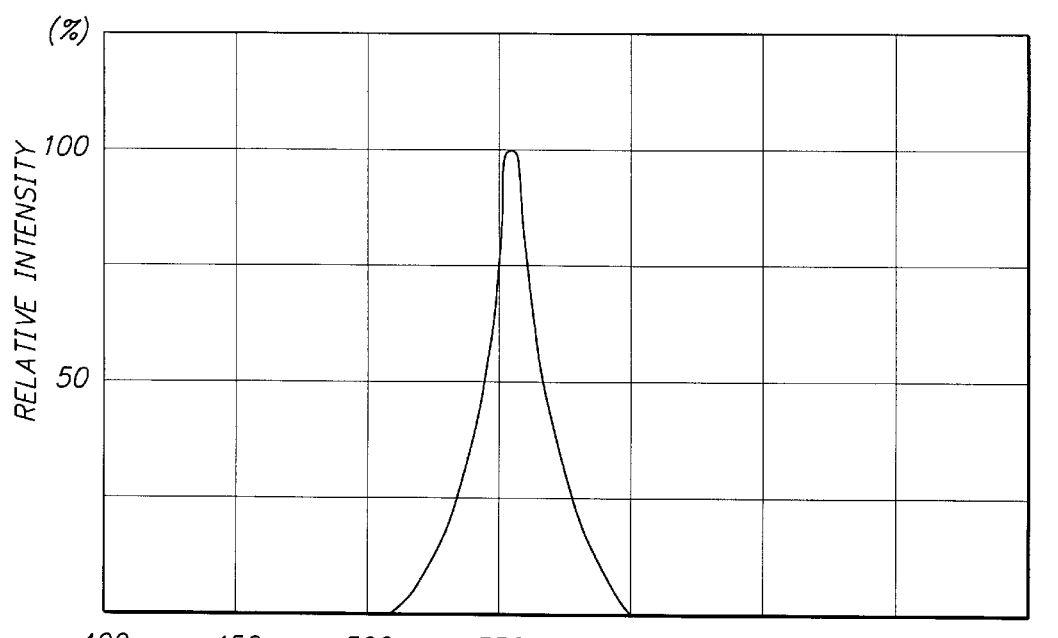
FIG. 17 is an explanatory graph showing light emission spectrum of a GaP type LED for use in the arm wear type pulse-wave measuring apparatus shown in FIG. 1.

The arm wear type pulse-wave measuring apparatus 1 according to this embodiment and the conventional pulse-wave measuring apparatus (the comparative example) were used to compare and investigate the pulse wave signal level ($\mu A$), the overall level of reflected light ($\mu A$) and the ratio of the pulse wave signal included in reflected light, results being shown in Table 2. As the pulse-wave measuring apparatus 1 according to this embodiment, sample 6 comprising the LED 31 (that emits blue light) having the light emission wavelength region of 420 nm to 480 nm; and sample 7 comprising the LED 31 (that emits green light) having the light emission wavelength region of 540 nm to 570 nm were evaluated. Sample 7 comprised the Gap type LED 31 that emits green light. The GaP type LED 31 had the light emission spectrum as shown in FIG. 17 such that the main light emission region was in a range from 540 nm to 570 nm and the light emission region was in a range from 520 nm to 600 nm. Sample 7 comprising the foregoing GaP type LED 31 comprised the GaP type phototransistor 32 to be adaptable to the light emission characteristics of the LED 31. The GaP type phototransistor 32 had the light receiving sensitivity such that the sensitive region existed in a range from 200 nm to near 700 nm, as shown in FIG. 18.

As comparative examples, samples 8, 9 and 10 each having the light emission wavelength region that was out of the range from 300 nm to 700 nm were evaluated.

Table 2 showed results of the evaluation.

TABLE 2

| | Structure of Sensors According to Examples | | Structure of Sensors According to Comparative Examples | | |
|---|---|---|---|---|---|
| Samples | Sample 6 | Sample 7 | Sample 8 | Sample 9 | Sample 10 |
| Light Emission Region | 420 nm to 480 nm | 540 nm to 570 nm | 800 nm to 850 nm | 850 nm to 900 nm | 900 nm to 970 nm |
| Items | | | | | |
| Level of Pulse Wave Signal ($\mu A$) | 0.12 | 0.10 | 0.04 | 0.07 | 0.06 |
| Level of Reflected light ($\mu A$) | 6.32 | 7.42 | 29.4 | 36.2 | 31.1 |
| Ratio of Pulse Wave Signal in Reflected Light | 0.019 | 0.013 | 0.0014 | 0.0019 | 0.0019 |

As shown in Table 2, the arm wear type pulse-wave measuring apparatus 1 (samples 6 and 7) according to this embodiment uses light having the light emission wavelength region of 300 nm to 700 nm to be adaptable to the wavelength region in which the light absorption factor of hemoglobin in the blood is large. Therefore, high ratios of pulse wave signals included in reflected light of 0.019 and 0.013 are attained, that is, excellent sensitivity can be obtained. As contrasted with this, the pulse-wave measuring apparatuses according to the comparative examples (samples 8, 9 and 10) has low ratios of the pulse wave signals included in reflected light of 0.002 or lower, that is, the sensitivity is unsatisfactory. Namely, the sensitivity of the arm wear type pulse-wave measuring apparatus 1 according to this embodiment can be significantly improved such that the S/N ratio of the pulse wave signal can be raised to about 10 times that of the conventional structure.

Influence of Skin Color

Results of investigation that the advantage of the significant sensitivity of the arm wear type pulse-wave measuring apparatus 1 according to this embodiment is not affected by the skin color are shown in Table 3. The evaluation was performed by using the arm wear type pulse-wave measuring apparatus 1 (sample 11) comprising the LED (the blue light source) having the light emission wavelength peak of 450 nm that could not easily be reflected by the surface of the skin; and the conventional pulse-wave measuring apparatus (comparative example and sample 12) comprising the LED having the light emission wavelength peak of 880 nm that could easily be reflected by the surface of the skin. The pulse waves of the yellow-skinned races, white races and the black races were measured to calculate the quantity of reflection of light from the skins, the quantity of reflection of light from the organisms (the quantity of light from the blood vessels) and pulse wave components.

TABLE 3

| Races/Samples Items | The Yellow-Skinned Races | | The White Races | | The Black Races | |
|---|---|---|---|---|---|---|
| | Example Sample 11 | Comparative Example Sample 12 | Example Sample | Comparative Example Sample 12 | Example Sample 11 | Comparative Example Sample 12 |
| Wavelength of LED (nm) | 450 | 880 | 450 | 880 | 450 | 880 |
| Quantity of Irradiation with Light from LED ($\mu$A) | 100 | 100 | 100 | 100 | 100 | 100 |
| Quantity of Reflection from Skin (1) ($\mu$A) | 14.0 | 35.0 | 28.0 | 35.0 | 9.3 | 21.0 |
| Quantity of Reflection from Organism (2) ($\mu$A) | 15.9 | 24.5 | 19.6 | 24.5 | 8.4 | 29.4 |
| Pulse Component ($\mu$A) | 0.31 | 0.01 | 0.39 | 0.01 | 0.17 | 0.02 |
| Total Quantity of Received Light (1 + 2) ($\mu$A) | 29.9 | 59.5 | 47.6 | 59.5 | 17.7 | 50.4 |

As a result, as shown in Table 3, a fact was confirmed that the ratio of the pulse wave components with respect to the overall quantity of received light was high, that is, the measuring sensitivity with respect to information about the organism was excellent in any of the cases where the yellow-skinned races, whites and the blacks were made to be the subjects.

Other Embodiments

The sensor unit according to the present invention can be put on another finger (the thumb, the middle finger, the ring finger or the little finger) as well as on the forefinger. If the sensor unit is put on any finger, the user is able to lightly clench the fist with the sensor unit put on the finger. Therefore, the user is able to select the finger on which the sensor unit is put as desired.

As the means for transmitting the result of receipt of light (the signal) from the light receiving portion of the sensor unit to the body of the pulse-wave measuring apparatus, a wireless method may be employed in place of the wired method typified by the cable 20 according to the foregoing embodiment. That is, a transmission circuit is included in the sensor unit or the sensor securing band or the like, on which the sensor unit is mounted; and a receiving circuit is included in the body of the apparatus. In the case of the arm wear type pulse-wave measuring apparatus according to the present invention, the distance from the transmitting portion (the root of the finger) to the receiving portion (arm) is very short so that only a very weak output of electric waves is required. Therefore, a very small transmission circuit/receiving circuit can be formed. A portion or the overall body of the sensor securing band may be used as an antenna of the transmission circuit.

Information about an organism except the pulse waves is exemplified as follows.

Since the light absorption characteristics of hemoglobin in the blood is, as shown in FIG. 12(b), different between hemoglobin, that has not been bonded with oxygen, and hemoglobin that has been bonded with oxygen, use of light having the wavelength from 300 nm to 700 nm, for example, about 470 nm, as detection light enables the quantity of each hemoglobin and the total quantity of hemoglobin to be measured as information about an organism in accordance with the intensity of the detection light. Furthermore, the difference in the light absorption characteristic between the skin and water can be used to measure water contained in the skin as information about an organism.

As described above, the arm wear type pulse-wave measuring apparatus (the organism information measuring apparatus) according to the present invention is characterized in that the fingertip or the like is irradiated with light by the light emitting portion, such as the LED; reflected light from the blood or the like is detected by the light receiving portion, such as the transistor; information about an organism is measured in accordance with results of detection in the wavelength region from 300 nm to 700 nm obtained by the foregoing detection means. When the detection in the foregoing wavelength region is performed, determination of the wavelength region of the light emitting portion to be at least in the range from 300 nm to 700 nm and the light receiving wavelength region to be 700 nm or shorter causes light included in external light that has the wavelength region of 700 nm or shorter not to reach the light receiving portion through the finger serving as the photoconductor. On the other hand, light in the wavelength region shorter than 300 nm is substantially completely absorbed by the surface of the skin. Therefore, the results of the detection is not affected by external light, and information about an organism can be measured in accordance with the result of detection in the wavelength region from 300 nm to 700 nm according to only light from the light emitting portion. Thus, if external light is not directly made incident on the detection portion, erroneous detection of pulse waves occurring due to external light can be prevented. Thus, a large-scale light shielding structure is not required.

Therefore, the size of the sensor unit can be reduced to the size that enables the sensor unit to be put on the root of the finger. The foregoing small sensor unit enables the user to lightly clench the fist with the sensor unit put on, whereby no problem arises to perform exercise, such as jogging, running or cycling. As a result, the foregoing sensor unit is suitable when the pulse rate or the like is measured during exercise, such as jogging.

Since the bloodstream is not relatively reduced in the root of the finger, the sensor unit put on the root of the finger enables the pulse rate or the like to be measured accurately even if a user performs exercise in a cold day.

Hemoglobin in the blood has a light absorption factor with respect to light having the wavelength region in a range from 300 nm to 700 nm that is considerably larger than the light absorption factor with respect to infrared rays. When light, the wavelength region of which is in the range from 300 nm to 700 nm, is applied toward an organism to be adaptable to the light absorption characteristic of hemoglobin, the intensity of light reflected by the organism (the blood vessel) is considerably changed to follow the change in the quantity of blood. As a result, the S/N ratio of the pulse wave signal can be raised so that an effect is obtained with the arm wear type pulse-wave measuring apparatus according to the present invention in that excellent sensitivity can be attained in measuring the pulse waves.

By employing the InGaN (Indium-Gallium-Nitrogen) type blue LED as the light emitting portion and by employing the GaAsP (Gallium-Arsenic-phosphorus) type phototransistor as the light receiving portion, excellent measuring sensitivity can be attained and the electric current consumption can be reduced so that measurement for a long time is preferably performed. Thus, the structure of the present invention is suitable to form a portable pulse-wave measuring apparatus (organism information measuring apparatus) of an arm wear type according to the present invention, the power source of which is limited.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

What is claimed is:

1. A method of operating an arm wear type pulse-wave measuring device, comprising:

securing a sensor means to a band, mounting said band on a region from a root of a finger to a joint of said finger such that a light receiving surface of a light receiving means and a light emitting surface of a light emitting means face a surface of said finger, emitting and detecting light from said sensor means, said emitting and detecting light step including irradiating said surface of said finger with light from said light emitting means, receiving light emitted by said light emitting means and reflected by said finger with said light receiving means, and producing detection results based on said received light, transmitting said detection results produced by said light receiving means to a pulse-wave measuring means;

measuring pulse waves, and displaying information about pulse waves in accordance with said detection results produced by said light receiving means, and wherein said light emitting step includes emitting light having a wavelength in a range from 350 nm to 600 nm, and said light receiving step includes receiving light having a wavelength $\lambda$ nm in a range that satisfies the following expression:

$$0 < \lambda \leq 700.$$

2. A method of operating an arm wear type pulse-wave measuring device as in claim 1 wherein said emitting and detecting light step includes emitting light from an LED (Light Emitting Diode).

3. A method of operating an arm wear type pulse-wave measuring device as in claim 2 wherein said emitting and detecting light step includes emitting light from an InGaN type (Indium-Gallium-Nitrogen type) blue LED.

4. A method of operating an arm wear type pulse-wave measuring device as in claim 1 wherein said emitting and detecting light step includes detecting light with a GaAsP type (Gallium-Arsenic-Phosphorus type) phototransistor.

5. A method of operating an arm wear type pulse-wave measuring device as in claim 1 wherein said securing a sensor means step includes securing said sensor means in a hole in said band.

* * * * *

UNITED STATES PATENT AND TRADEMARK OFFICE
CERTIFICATE OF CORRECTION

PATENT NO.     : 5,906,582
DATED          : May 25, 1999
INVENTOR(S)    : Yutaka Kondo, et al.

It is certified that an error appears in the above identified patent and that said Letters Patent is hereby corrected as shown below:

Title page, item 73, Assignee, change "Seiko Epson Corporation; Seiko Instruments, Inc., both of Tokyo, Japan" to --Seiko Epson Corporation, Tokyo; Seiko Instruments, Inc., Chiba-ken, both of Japan--.

Signed and Sealed this

Twenty-second Day of February, 2000

Attest:

Q. TODD DICKINSON

*Attesting Officer*            *Commissioner of Patents and Trademarks*